US012708596B2

(12) United States Patent
Yang et al.

(10) Patent No.: US 12,708,596 B2
(45) Date of Patent: Aug. 18, 2026

(54) COSMETIC CLEANSING COMPOSITION

(71) Applicant: SHISEIDO COMPANY, LTD., Tokyo (JP)

(72) Inventors: Binhua Yang, East Windsor, NJ (US); Maria Barsom, East Windsor, NJ (US)

(73) Assignee: SHISEIDO COMPANY, LTD., Tokyo (JP)

( * ) Notice: Subject to any disclaimer, the term of this patent is extended or adjusted under 35 U.S.C. 154(b) by 287 days.

(21) Appl. No.: 18/522,783

(22) Filed: Nov. 29, 2023

(65) Prior Publication Data

US 2025/0170039 A1 May 29, 2025

(51) Int. Cl.

| | |
|---|---|
| ***A61K 8/36*** | (2006.01) |
| ***A61K 8/44*** | (2006.01) |
| ***A61K 8/46*** | (2006.01) |
| ***A61K 8/49*** | (2006.01) |
| ***A61Q 5/02*** | (2006.01) |

(52) U.S. Cl.

CPC .............. *A61K 8/361* (2013.01); *A61K 8/442* (2013.01); *A61K 8/447* (2013.01); *A61K 8/466* (2013.01); *A61K 8/498* (2013.01); *A61Q 5/02* (2013.01); *A61K 2800/262* (2013.01); *A61K 2800/30* (2013.01)

(58) Field of Classification Search

CPC ........ A61K 8/361; A61K 8/442; A61K 8/447; A61K 8/466; A61K 8/498; A61K 2800/262; A61K 2800/30; A61K 8/84; A61K 8/345; A61K 8/44; A61Q 5/02; A61Q 19/10

See application file for complete search history.

(56) References Cited

U.S. PATENT DOCUMENTS

| | | | | |
|---|---|---|---|---|
| 6,627,612 | B1 | 9/2003 | O'Lenick, Jr. et al. | |
| 2016/0296446 | A1* | 10/2016 | Tanavade | A61Q 19/10 |
| 2017/0128407 | A1 | 5/2017 | Shalviri et al. | |
| 2020/0306151 | A1* | 10/2020 | Takahashi | A61K 8/39 |
| 2022/0117881 | A1* | 4/2022 | Nakano | A61K 8/37 |
| 2022/0259521 | A1 | 8/2022 | Comber et al. | |

FOREIGN PATENT DOCUMENTS

| | | | | |
|---|---|---|---|---|
| CN | 108066164 B | | 6/2020 | |
| EP | 1057888 A2 | * | 12/2000 | C11D 10/042 |
| EP | 3 373 928 B1 | | 10/2021 | |
| JP | 2002-080897 A | | 3/2002 | |
| KR | 10-2017-0135654 A | | 12/2017 | |
| WO | WO-2022233624 A1 | * | 11/2022 | A61K 8/466 |

OTHER PUBLICATIONS

International Searching Authority, "International Search Report and Written Opinion," issued in connection with International Patent Application No. PCT/IB2024/061879 dated Mar. 12, 2025.

* cited by examiner

*Primary Examiner* — Mark V Stevens
*Assistant Examiner* — Arya Ahmadi Bazargani
(74) *Attorney, Agent, or Firm* — Foley & Lardner LLP

(57) ABSTRACT

Provided is a cosmetic composition that includes: (a) at least one surfactant, which includes at least one anionic surfactant; and (b) a fatty acid thickener. The cosmetic composition may be transparent and sulfate free.

16 Claims, 4 Drawing Sheets

COSMETIC CLEANSING COMPOSITION

FIELD

The present disclosure relates in general to cosmetic compositions, their uses and their methods of making.

SUMMARY

According to an embodiment, a cosmetic composition comprises (a) at least one surfactant, which comprises at least one anionic surfactant; and (b) at least one fatty acid thickener, wherein the cosmetic composition is transparent and sulfate free.

FIGURES

DETAILED DESCRIPTION

Figure 1:
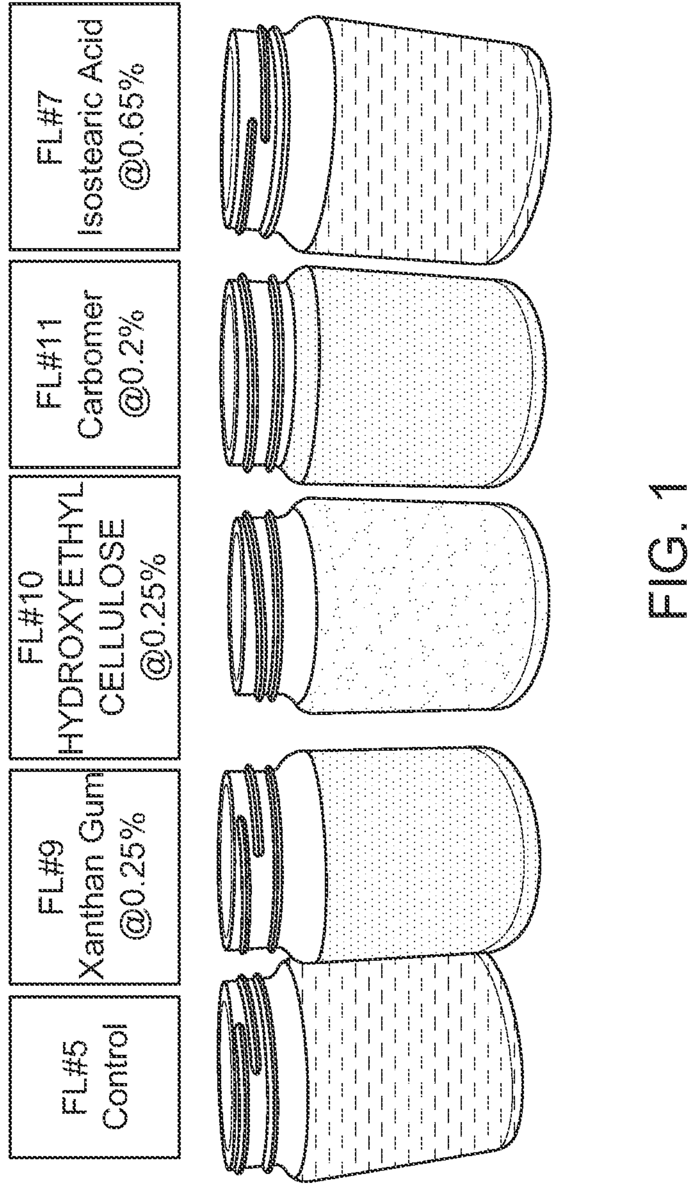
FIG. 1 is five formulations right after the formulations were prepared.

Unless otherwise specified "a" or "an" means one or more.

As used herein, the term "about" placed before a specific numeric value may mean ±20% of the numeric value; ±18% of the numeric value, ±15% of the numeric value; ±12% of the numeric value; ±8% of the numeric value; ±5% of the numeric value; ±3% of the numeric value; ±2% of the numeric value; ±1% of the numeric value or ±0.5% of the numeric value.

Each numeric value in this disclosure should be treated as being preceded by the term "about".

Unless otherwise specified, all content information for ingredients of compositions expressed as % refers to % by mass, relative to the total mass of the composition, unless specified otherwise.

Cosmetic cleansing formulations often contain sulfate-based surfactants. However, sulfate-based surfactants may be aggressive on the skin. For example, sulfate-based surfactants may strip of the skin's natural oils, which may make the skin too dry. Therefore, many consumers prefer cosmetic products that do not contain sulfate-base surfactants. However, a sulfate-free cleansing formulation, i.e. a cleansing formulation that is free of sulfate containing ingredients, including sulfate-based surfactants, may be difficult to thicken sufficiently to have good sensory properties. Many sulfate-free cleansing formulations do not remain on a consumer's face during or after application due to insufficient viscosity and/or thickening. The dripping and running during the application of many sulfate-free cleansing formulations often leads to an unpleasant experience by users of such formulations.

Currently, there may be two approaches for thickening sulfate-free cleanser formulations. One is using higher concentration(s) of sulfate-free surfactant(s) to benefit the self-assembly properties. Although such approach is very common, but it is also costly. The second approach is using high concentrations of rheological modifiers. However, this can negatively impact the cleanser formulation performance by, for example, decreasing a foaming ability of the formulation. This approach is also costly.

Thus, while there are several classes of surfactants, which may be a suitable replacement for sulfated products, it may be challenging to increase a viscosity of a sulfate-free cosmetic composition. Sulfate-free surfactants can be difficult to thicken because many of them do not form micelle structures in the way anionic sulfate surfactants do. Sulfate-free surfactants have also a poor response to salt thickening.

A further challenge may be making such that a sulfate-free composition is clear and/or transparent while at the same time increasing its viscosity. It is difficult to find a thickening agent that make the composition thicker or more viscous while maintaining a clarity of the composition.

The present disclosure addresses these challenges.

The present disclosure provides a sulfate-free cosmetic composition that is clear and/or transparent. The formulation includes (a) at least one surfactant, which includes at least one anionic surfactant; and (b) a fatty acid thickener.

In many embodiments, the present cosmetic composition may be silicone-free, i.e. free of any silicone containing ingredients.

In many embodiments, the present cosmetic composition may be polyethylene glycol (PEG)-free, i.e. free of any ingredients containing PEG.

In many embodiments, the present composition may be transparent. As used herein, the term "transparent" may mean than a sample of the composition exhibits a transmittance of at least 80%, at least 81%, at least 82%, at least 83%, at least 84% or at least 85% compared that of a water sample of an identical size at a wavelength in a range from 400 nm to 800 nm. For example, a sample of the composition may exhibit a transmittance of at least 80%, at least 81%, at least 82%, at least 83%, at least 84% or at least 85% compared to that of a water sample of an identical size at a wavelength of 550 nm.

In many embodiments, the present cosmetic composition may have a crystal clear (i.e. transparent to a human eye similarly to water) jelly (i.e. gel-like thick consistency) texture.

In many embodiments, the present cosmetic composition may have a viscosity at about 12 rpm from about 3000 cps to about 11000 cps or from about 3600 cps to about 10000 cps or from about 4000 cps to about 11000 cps or from about 4500 cps to about 10500 cps or from about 5000 cps to about 10000 cps. In many embodiments, the present cosmetic composition may be stable to maintain a viscosity within such ranges for at least 1 week, at least 2 weeks or at least 4 weeks of storing at any temperature from about −5° C. to about 50° C. or at any temperature from 0° C. to 50° C.

In many embodiments, the present cosmetic composition has a good cleansing performance along with a good sensory performance. The good cleansing may mean that the composition acts as a mild cleanser; being easy to wash and being able to remove light makeups, leaving no residue on the skin and no irritation after washing, even in the eye area, while clearing pores. The good sensory performance may mean that after the application of the composition to the skin, the skin does not feel dry and/or tight after using, the skin feels fresh, moisturized and soothed, no irritation; the skin becomes softer, healthier.

In many embodiments, the present cosmetic composition have pH from about 5.0 to about 5.5 or from about 5.1 to about 5.5 or from about 5.1 to about 5.4 or from about 5.2 to about 5.4. In many embodiments, the present cosmetic composition may be stable to maintain pH within such ranges for at least 1 week, at least 2 weeks or at least 4 weeks of storing at any temperature from about −5° C. to about 50° C. or at any temperature from 0° C. to 50° C.

Compared to existing sulfate-free cleanser formulations, such as formulations prepared using the discussed above approaches for thickening sulfate-free cleanser formulations, the present cosmetic composition may be more cost-friendly.

In some embodiment, the composition may be a cleansing composition, which may be applied to a skin of a subject, such as a human. In some embodiments, the composition may be a facial cleansing composition, which may be applied to a face of a subject, such as a human.

In some embodiments, applications of the cosmetic composition may include but are not limited to applications in a skin care product, such as a cleanser for face and/or body, or in a hair product, such as a shampoo.

Fatty Acid Thickener

In cosmetic products, a thickener or a thickening agent is an ingredient that can enhance consistency, volume and/or viscosity of a cosmetic composition.

The present cosmetic composition contains at least one fatty acid thickener. As used herein, the term "fatty acid thickener" may refer to a thickening agent that is a fatty acid, which may be saturated or unsaturated, branched or straight chained), or a source of fatty acids, and mixtures thereof. Fatty acid thickeners are disclosed, for example, in EP3373928 and US20170128407, each of which is incorporated herein by reference in its entirety.

Preferably, the fatty acid thickener is a fatty acid that is in a liquid state at a room temperature, such as about 20° C.

Exemplary fatty acid thickeners include, but are not limited to, isostearic acid, linoleic acid, linolenic acid, oleic acid and mixtures thereof.

An amount of the at least one fatty acid thickener in the present cosmetic composition may vary. For example, in some embodiments, the present composition may contain from about 0.1% to about 1.5% or from about 0.1% to about 1.2% or from about 0.2% to about 1.0% or from about 0.3% to about 1.0% or from about 0.3% to about 0.8% of the at least one fatty acid thickener.

In some embodiments, the at least one fatty acid thickener may comprise isostearic acid. Without being limited by theory, in some embodiments, isostearic acid may act as a co-surfactant.

An amount of isostearic acid in the present cosmetic composition may vary. For example, in some embodiments, the present composition may contain from about 0.2% to about 1.5% or about 0.2% to about 1.2% or from about 0.2% to about 1.0% or from about 0.3% to about 0.8% of isostearic acid.

In some embodiments, the cosmetic composition may contain no other thickener other than a fatty acid thickener, such as isostearic acid.

Sulfate-Free Surfactant(s)

The present cosmetic composition includes at least one sulfate-free surfactant, which may include at least one sulfate-free anionic surfactant.

In some embodiments, the at least one sulfate-free anionic surfactant may include at least one anionic alkyl glucoside (AG) derivative surfactant. In some embodiments, the at least one anionic alkyl glucoside (AG) derivative surfactant may be an alkylglycoside sulfonate, an alkylpolyglycoside sulfonate, or an alkylpolyglycoside phosphate. In some embodiments, the anionic alkylglucoside (AG) derivative may be one or more of Sodium Laurylglucoside Hydroxypropylsufonate, Sodium Decylglucoside Hydroxypropylsufonate, Sodium Hydroxypropylphosphate Laurylglucoside Crosspolymer, Sodium Hydroxypropylphosphate Decylglucoside Crosspolymer, or a combination or mixture thereof. In some embodiments, the anionic AG derivative surfactant may be Sodium Laurylglucoside Hydroxypropylsufonate or Sodium Decylglucoside Hydroxypropylsufonate, or a mixture thereof. In some embodiments, the anionic AG derivative surfactant may be Sodium Hydroxypropylphosphate Laurylglucoside Crosspolymer, or Sodium Hydroxypropylphosphate Decylglucoside Crosspolymer, or a mixture thereof. In some embodiments, the anionic AG derivative surfactant may be Sodium Laurylglucoside Hydroxypropylsufonate and Sodium Hydroxypropylphosphate Laurylglucoside Crosspolymer.

Alkyl glucoside (AG) derivative surfactants are disclosed, for example, in US20170128407 and US20220259521, which are incorporated herein by reference in their entirety.

Alkyl glucoside (AG) derivative surfactants, such as alkyl polyglucoside surfactants, are commercially available, for example, from Colonial Chemical, Inc. Two examples of which are sodium laurylglucosides hydroxypropylsulfonate (sold under the brand name Poly Suga® Nate 160NC) and sodium decylglucosides hydroxypropylsulfonate (sold under the brand name Poly Suga® Nate 100NC).

These surfactants are synthesized by the methods outlined in U.S. Pat. No. 6,627,612 or their corresponding patents and are generally supplied as clear solutions, 30-50 percent solids, that may be used as is in emulsion polymerization reactions.

Poly Suga® Nate 160NC contains around 40% solids that correspond to SODIUM HYDROXYPROPYLSULFONATE LAURYLGLUCOSIDE CROSSPOLYMER.

An amount of the anionic alkyl glucoside surfactant, such as an anionic alkyl polyglucoside surfactant, in the cosmetic composition may vary. In some embodiments, the cosmetic composition may contain from at least 0.5% to 10% or from at least 2% to 6% or from at least 0.5% to 6% or from at least 0.8% to at least 6% or from at least 1% to at least 6% of the anionic alkyl glucoside surfactant, such as an anionic alkyl polyglucoside surfactant.

In some embodiments, a mass ratio between a content of the anionic alkyl glucoside surfactant, such as an anionic alkyl polyglucoside surfactant, and a content of a fatty acid thickener, such as isostearic acid, in the composition may be from 0.3 to 50 or from 0.5 to 50 or from 1 to 20 or from 2.5 to 20 or any value or subrange within these ranges.

In some embodiments, the cosmetic composition may contain sodium hydroxypropylsulfonate laurylglucoside crosspolymer as an anionic alkyl glucoside surfactant.

An amount of hydroxypropylsulfonate laurylglucoside crosspolymer in the cosmetic composition may vary. In some embodiments, the cosmetic composition may contain from at least 0.5% to 10% or from at least 2% to 8% or from at least 0.5% to 8% or from at least 0.8% to at least 8% or from at least 1% to at least 8% of hydroxypropylsulfonate laurylglucoside crosspolymer.

In some embodiments, a mass ratio between a content of hydroxypropylsulfonate laurylglucoside crosspolymer and a content of a fatty acid thickener, such as isostearic acid, in the composition may be from 0.3 to 50 or from 0.5 to 50 or from 1 to 30 or from 2.5 to 30 or from 2.5 to 27 or any value or subrange within these ranges.

In some embodiments, the at least one anionic surfactant may further include at least one taurate anionic surfactant. Taurate anionic surfactant includes a hydrophilic head group of N-methyltaurine (2-methylaminoethanesulfonic acid) and a lipophilic residue, which may include or consist of a long-chain carboxylic acid (fatty acid), both linked via an amide bond. Fatty acids in taurate surfactants include, but are not limited to, lauric (C12), myristic (C14), palmitic (C16) or stearic acid (C18), including mixtures thereof, such as a mixtures of oleic acid (C18:1) and coconut fatty acid (C8-C18) are used. The counterion in taurate anionic surfactants is usually sodium. In some embodiments, the counterion in a taurate anionic surfactant may be another alkali metal, ammonium or an alkaline earth metal.

One non-limiting example of a taurate anionic surfactant is Sodium Methyl Cocoyl Taurate. For example, commercially available PUREACT WS CONC contains 70% WATER & 30% SODIUM METHYL COCOYL TAURATE.

An amount of the at least one taurate anionic surfactant, such as Sodium Methyl Cocoyl Taurate, in the cosmetic composition may vary. For example, in some embodiments, the cosmetic composition may contain from 0.5% to 6% or from 1% to 5% or from 1% to 3% of the at least one taurate anionic surfactant, such as Sodium Methyl Cocoyl Taurate.

In some embodiments, a mass ratio between a content of the at least one taurate anionic surfactant, such as Sodium Methyl Cocoyl Taurate, and a content of a fatty acid thickener, such as isostearic acid, in the composition may be from 0.3 to 30 or from 0.5 to 30 or from 1 to 20 or from 1.3 to 10 or any value or subrange within these ranges.

In some embodiments, a mass ratio between a content of the at least one taurate anionic surfactant, such as Sodium Methyl Cocoyl Taurate, and the anionic alkyl glucoside surfactant, such as an anionic alkyl polyglucoside surfactant, in the composition may be from 0.1 to 12 or 0.1 to 10 or 0.1 to 5 or 0.1 to 3 or 0.1 to 2 or 0.1 to 1.5 or any value or subrange within these ranges.

In some embodiments, the cosmetic composition may include at least one non-ionic surfactant in addition to the at least one anionic surfactant. Non-limiting examples non-ionic surfactants include decyl glucoside, coco glucoside, lauryl glucoside or a mixture thereof.

Coco glucoside is commercially available in PLANTAREN® 818 UP, which contains 51-55% COCO-GLUCOSIDE.

An amount of the at least one non-ionic surfactant, such as coco glucoside, in the cosmetic composition may vary. For example, in some embodiments, the cosmetic composition may contain from 1% to 6% or from 1% to 5% or from 2% to 5% or from 1.5% to 5% of the at least one non-ionic surfactant, such as coco glucoside.

In some embodiments, a mass ratio between a content of the at least one non-ionic surfactant, such as coco glucoside, and a content of a fatty acid thickener, such as isostearic acid, in the composition may be from 0.7 to 30 or from 1 to 20 or from 2 to 17 or from 2.5 to 17 or any value or subrange within these ranges.

In some embodiments, a mass ratio between a content of the at least one non-ionic surfactant, such as coco glucoside, and a content of the at least one anionic surfactant, in the composition may be 0.2 to 12 or 0.5 to 10 or 0.7 to 5 or any value or subrange within these ranges.

In some embodiments, the cosmetic composition may include at least one amphoteric surfactants in addition to the at least one anionic surfactant.

In some embodiments, the at least one amphoteric surfactant may include at least one betaine surfactant, such as cocamidopropyl betaine. Cocamidopropyl betaine is commercially available in TRITEXAINE CB-HP, which contains around 30.5% of COCAMIDOPROPYL BETAINE.

An amount of the at least one betaine surfactant, such as cocamidopropyl betaine, in the cosmetic composition may vary. For example, in some embodiments, the cosmetic composition may contain 0.5% to 5% or from 0.5% to 4% or from 1% to 4% or from 1% to 3.5% or from 1% to 3% of the at least one betaine surfactant, such as cocamidopropyl betaine.

In some embodiments, a mass ratio between a content of the at least one betaine surfactant, such as cocamidopropyl betaine, and a content of a fatty acid thickener, such as isostearic acid, in the composition may be 0.3 to 25 or 1 to 20 or 1.3 to 10 or any value or subrange within these ranges.

In some embodiments, a mass ratio between a content of the at least one betaine surfactant, such as cocamidopropyl betaine, and a content of the at least one anionic surfactant, in the composition may be 0.1 to 10 or 0.2 to 5 or 0.3 to 3 or any value or subrange within these ranges.

In some embodiments, the at least one amphoteric surfactant may contain cocamidopropyl hydroxysultaine. Cocamidopropyl hydroxysultaine is commercially available in COLA®TERIC CBS-HP MB, 48-50% of solids, including COCAMIDOPROPYL HYDROXYSULTAINE.

An amount of cocamidopropyl hydroxysultaine in the cosmetic composition may vary. For example, in some embodiments, the cosmetic composition may contain 5% to 20% or from 5% to 18% or from 5% to 15% or from 5% to 12% of cocamidopropyl hydroxysultaine.

In some embodiments, a mass ratio between a content of cocamidopropyl hydroxysultaine and a content of a fatty acid thickener, such as isostearic acid, in the composition may be 3 to 100 or 5 to 80 or 6 to 70 or 6 to 60 or 6 to 40 or any value or subrange within these ranges.

In some embodiments, the at least one amphoteric surfactant may contain at least two amphoteric surfactants. For example, in some embodiments, the cosmetic composition may contain at least one betaine surfactant, such as cocamidopropyl betaine, and cocamidopropyl hydroxysultaine.

In some embodiments, the cosmetic composition may include at least one anionic surfactant, at least one non-ionic surfactant and at least one amphoteric surfactant. In some embodiments, the cosmetic composition may include at least two anionic surfactants, at least one non-ionic surfactant and at least one amphoteric surfactant. In some embodiments, the cosmetic composition may include at least one anionic surfactant, at least one non-ionic surfactant and at least two amphoteric surfactants. In some embodiments, the cosmetic composition may include at least two anionic surfactants, at least one non-ionic surfactant and at least two amphoteric surfactants.

In some embodiments, the composition may include an anionic alkyl glucoside surfactant, such as sodium hydroxypropylsulfonate laurylglucoside crosspolymer, an anionic taurate surfactant, such as Sodium Methyl Cocoyl Taurate, a sulfate-free non-ionic surfactant, such as coco glucoside, a betaine surfactant, such as cocamidopropyl betaine, and cocamidopropyl hydroxysultaine.

Other exemplary amphoteric surfactants include C12-14 alkyl betaine, C12-18 alkyl betaine, Cocoalkyl betaine, Cocoalkyl amidopropyl betaine, C14-15 hydroxysulfo betaine and Cocoalkyl hydroxysulfo betaine.

In many embodiments, the composition may be free of any cationic surfactants.

Solvent

The cosmetic composition may include at least 35% or at least 40% of water. For example, in some embodiments, the composition may include from 35% to 70% or from 40% to 70% or from 45% to 70% or from 50% to 70% or from 55% to 70% or from 60% to 70% of water.

Additional Ingredients

In some embodiments, the cosmetic composition may also include additional ingredient(s), such as emollient(s), such as glycerin; preservative(s), such as phenoxyethanol; neutralizing agent(s), such as citric acid. A total content of the additional ingredient(s) may be from 1 mass % to 20 mass % or from 5 mass % to 20 mass % or from 1 mass % to 15 mass % or from 2 mass % to 13 mass % or from 3 mass % to 10 mass % or from 4 mass % to 8 mass %.

Exemplary Composition

One exemplary cosmetic composition may contain (a) about 0.3 mass % to about 0.8 mass % of isostearic acid; (b) about 2 mass % to about 8 mass % Sodium Hydroxypropylsulfonate Laurylglucoside Crosspolymer; (c) about 2.5 mass % to about 5 mass % of coco-glucoside; (d) 1 mass % to 3 mass % of cocamidopropyl betaine and (e) at least 40 mass % of water. The composition may further contain (f) about 1 mass % to about 3 mass % of a taurate surfactant and (g) 5 mass % to 12 mass % of cocamidopropyl hydroxysultaine.

Method of Making

The composition may be prepared by adding water to a first container, which may be mixed, using for example, a propeller. The content of a first container may be heated to for example, a temperature in a range 65 C to 75 C.

One or more emollients, such as glycerine, and one or more preservative, such as phenoxyethanol, may be mixed in a second container.

The contents of the first container and the second container may be combined and mixed in a single container.

One or more fatty acid thickeners, such as isostearic acid, may be added to the single container during the mixing. The temperature in the single container may be maintained at, for example, 65 C to 75 C.

Each of surfactants may be added to the single container one by one, while mixing until the content is uniform after each addition and maintaining the temperature at 65 C to 75 C.

A neutralizing agent, such as anhydrous citric acid, may be added to adjust pH.

Embodiments described herein are further illustrated by, though in no way limited to, the following working examples.

Example 1

TABLE 1

Compositions of cleanser formulations with different thickeners

| Formulations Performance Comparison with Different Thickeners | | | FL #5 | FL #9 | FL #10 | FL #11 |
|---|---|---|---|---|---|---|
| Function | Trade Name | INCI Name | W/W % | W/W % | W/W % | W/W % |
| Solvent | DEIONIZED WATER | WATER | 42.84 | 43.03 | 39.95 | 43.15 |
| Emollient | GLYCERINE 99.7%/MB | GLYCERIN | 6.00 | 6.00 | 6.00 | 6.00 |
| Anionic Surfactants | PUREACT WS CONC | WATER & SODIUM METHYL COCOYL TAURATE | 8.00 | 8.00 | 8.00 | 8.00 |
| | POLY SUGA ®NATE 160P NC MB | WATER & SODIUM HYDROXYPROPYLSULFONATE LAURYLGLUCOSIDE CROSSPOLYMER & SODIUM CHLORIDE | 10.00 | 10.00 | 10.00 | 10.00 |
| Amphoteric Surfactant | TRITEXAINE CB-HP | WATER & COCAMIDOPROPYL BETAINE & SODIUM CHLORIDE & GLYCERIN | 5.00 | 5.00 | 5.00 | 5.00 |
| | COLA ®TERIC CBS-HP MB | WATER & COCAMIDOPROPYL HYDROXYSULTAINE & SODIUM CHLORIDE & TETRASODIUM GLUTAMATE DIACETATE | 20.00 | 20.00 | 20.00 | 20.00 |
| Non-ionic Surfactant | PLANTAREN ® 818 UP | COCO-GLUCOSIDE & WATER | 6.00 | 6.00 | 6.00 | 6.00 |
| Thickener | ISOSTEARIC ACID EX | ISOSTEARIC ACID | — | — | — | — |
| Thickener | NATROSOL ™ 250 HHX PHARM HYDROXYETHYLCELLULOSE | HYDROXYETHYLCELLULOSE & DISODIUM PHOSPHATE & SODIUM PHOSPHATE | — | — | 0.25 | — |
| | KELTROL T | XANTHAN GUM | — | 0.25 | — | — |
| | CARBOPOL 980 POLYMER | CARBOMER | — | — | — | 0.20 |
| Preservative | BOTANISTAT PF-64 | PHENOXYETHANOL & CAPRYLYL GLYCOL & ETHYLHEXYLGLYCERIN & HEXYLENE GLYCOL | 1.00 | 1.00 | 1.00 | 1.00 |
| | KALAMA ® SODIUM BENZOATE NF/FCC | SODIUM BENZOATE | 0.30 | 0.30 | 0.30 | 0.30 |
| pH adjust | CITRIC ACID ANHYDROUS (USP) (RM-253) | CITRIC ACID | 0.86 | 0.42 | 3.50 | 0.35 |
| | | Total | 100.00 | 100.00 | 100.00 | 100.00 |

TABLE 1-continued

| Compositions of cleanser formulations with different thickeners | | | | | | |
|---|---|---|---|---|---|---|
| Formulations Performance Comparison with Different Thickeners | | | FL #01 | FL # 02 | FL #06 | FL #07 |
| Function | Trade Name | INCI Name | W/W % | W/W % | W/W % | W/W % |
| Solvent | DEIONIZED WATER | WATER | 42.78 | 43.15 | 43.15 | 39.87 |
| Emollient | GLYCERINE 99.7%/MB | GLYCERIN | 6.00 | 6.00 | 6.00 | 6.00 |
| Anionic Surfactants | PUREACT WS CONC | WATER & SODIUM METHYL COCOYL TAURATE | 8.00 | 8.00 | 8.00 | 8.00 |
| | POLY SUGA ®NATE 160P NC MB | WATER & SODIUM HYDROXYPROPYLSULFONATE LAURYLGLUCOSIDE CROSSPOLYMER & SODIUM CHLORIDE | 10.00 | 10.00 | 10.00 | 10.00 |
| Amphoteric Surfactant | TRITEXAINE CB-HP | WATER & COCAMIDOPROPYL BETAINE & SODIUM CHLORIDE & GLYCERIN | 5.00 | 5.00 | 5.00 | 5.00 |
| | COLA ®TERIC CBS-HP MB | WATER & COCAMIDOPROPYL HYDROXYSULTAINE & SODIUM CHLORIDE & TETRASODIUM GLUTAMATE DIACETATE | 20.00 | 20.00 | 20.00 | 20.00 |
| Non-ionic Surfactant | PLANTAREN ® 818 UP | COCO-GLUCOSIDE & WATER | 6.00 | 6.00 | 6.00 | 6.00 |
| Thickener | ISOSTEARIC ACID EX | ISOSTEARIC ACID | — | — | 0.35 | 0.65 |
| Thickener | NATROSOL ™ 250 HHX PHARM HYDROXYETHYLCELLULOSE | HYDROXYETHYLCELLULOSE & DISODIUM PHOSPHATE & SODIUM PHOSPHATE | — | 0.50 | — | — |
| | KELTROL T | XANTHAN GUM | 0.50 | — | — | — |
| | CARBOPOL 980 POLYMER | CARBOMER | — | — | — | — |
| Preservative | BOTANISTAT PF-64 | PHENOXYETHANOL & CAPRYLYL GLYCOL & ETHYLHEXYLGLYCERIN & HEXYLENE GLYCOL | 1.00 | 1.00 | 1.00 | 1.00 |
| | KALAMA ® SODIUM BENZOATE NF/FCC | SODIUM BENZOATE | 0.30 | 0.30 | 0.30 | 0.30 |
| pH adjust | CITRIC ACID ANHYDROUS (USP) (RM-253) | CITRIC ACID | 0.42 | 0.35 | 0.35 | 3.18? |
| | | Total | 100.00 | 100.00 | 100.00 | 100.00 |

The compositions in Table 1 were prepared as follows:

Water was added to a main beaker and mixing started with a propeller. The content of the main beaker was heated up to 65-75 C. While Mixing, a designated thickener was added for each trial.

In a separate beaker, glycerin was mixed with the preservative until uniform. Then the content of the separate beaker was added to the main beaker.

Temperature was maintained at 65-75 C

Next each of surfactants was added to the main beaker one by one. After each addition, the content of the main beaker was mixed until uniform. The same temperature was maintained between the additions.

Citric acid anhydrous was added to the main beaker to adjust pH

Four different thickening agents were studied. They were used in the same formulation base with different concentrations. The composition of the cleanser formulations are listed in Table 1. The cleanser base comprises total three types of surfactants, including 6.4% anionic, 10.13% amphoteric, 3.3% non-ionic and they are all sulfate-free surfactants. The cleanser base also contains 6% emollient, preservatives and citric acid was used to adjust the pH~5.2.

The four thickening agents were compared using the same base cleanser compositions. The viscosity and clarity appearance of the cleanser formulations from Table 1 were compared and summarized in Table 2.

Viscosity was measured by Brookfield Ametek DV-I viscometer, Spindle LV #3, 12 rpm. However, formulation #1 and 2, were measured by spindle RV #5, 10 rpm.

pH measured by Thermo Scientific (Orion Star A 215) pH Conductivity Meter. Texture evaluated by inventors, by applying the FL sample on the face. Clarity was evaluated by inventor's eye and Transmittance % was measured by using HITACHI spectrophotometer U-3900H according to method ARD-03-108.

Transmittance is the percentage of light impinging on a solution that passes through the solution and emerges to be detected by the instrument. Transmittance % was scanned from 400 nm-800 nm wavelength and the values measured at 550 nm by HITACHI spectrophotometer U-3900H. Water was used as a standard.

It is zero for a completely opaque solution and 100% when all the light is transmitted.

TABLE 2

| Viscosity and Appearance (Clarity) Comparison for the formulations from Table 1. | | | | | |
|---|---|---|---|---|---|
| Formulation # | Thickener INCI Name | %, mass | Viscosity (RV#5, 10 rpm) | Visual Appearance Clarity | Texture |
| 5 | none | 0 | 3680 | Clear | Viscosity is too low |
| 9 | XANTHAN GUM | 0.25% | 6400 | Cloudy | OK |
| 1 | XANTHAN GUM | 0.50% | 20360 | Cloudy | Viscosity is too thick |
| 10 | HYDROXYETHYLCELLULOSE | 0.25% | 4670 | Cloudy | Viscosity is little low |
| 2 | HYDROXYETHYLCELLULOSE | 0.50% | 39440 | Cloudy | Viscosity is too thick |
| 11 | CARBOMER | 0.20% | 4670 | Hazy | Viscosity is little low |
| 6 | Isostearic Acid | 0.35% | 7000 | Clear | Good |
| 7 | Isostearic Acid | 0.65% | 8800 | Clear | Good |

Table 2 demonstrates that common thickeners, such as xanthan gum, hydroxyethylcellulose and carbomer, can increase the viscosity, while not yielding a desirable texture and clarity. The appearance of the formulations containing such common thickeners was cloudy and hazy.

It was surprisingly discovered that isosteric acid, which is a thickener also able to act as co-surfactant, thickens a cleanser to a desirable viscosity (thereby providing the desirable texture) while also providing a crystal clarity appearance for the cleanser.

Figure 2:
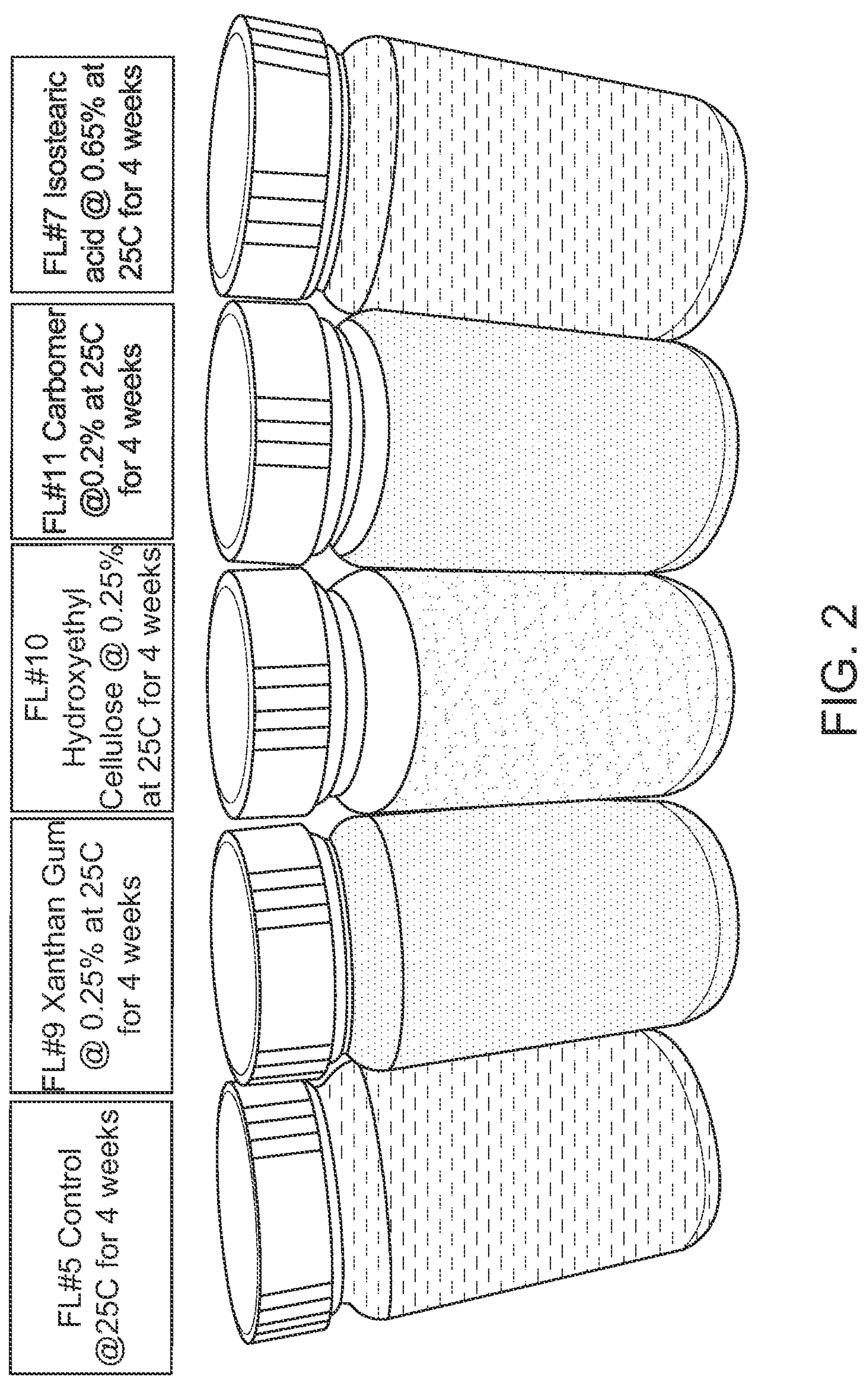
FIG. 2 shows the same five formulations as in FIG. 1 but after storing the formulations for 4 weeks at 25° C. after the formulations were prepared.

FIG. 1 is formulations 5, 9, 10, 11 and 7 right after the formulations were prepared. FIG. 2 is the same five formulations but after being stored for 4 weeks at 25° C. after the formulations were prepared. FIGS. 1 and 2 demonstrate that formulation 7 has the same crystal clear appearance as control formulation 5 and that formulation 7 maintained such appearance after being stored for 4 weeks at 25° C.

Transmittance (%) of each of five cleanser formulations, including four formulations with four different thickeners and a control formulation with no thickener, was measured using HITACHI spectrophotometer U-3900H.

Transmittance represents a fraction of incident light which is transmitted through a test substance, which is in the present case, a cleanser formulation. Transmittance % was measured in the range 400 nm-800 nm wavelength and the values of transmittance at 550 nm are presented in Table 3. Water was used as a standard.

TABLE 3

| Transmittance of Cleanser formulations | | | |
|---|---|---|---|
| Formulation # | Thickener INCI Name | Mass % Thickener | Transmittance, % |
| 5 | none | 0 | 87 |
| 6 | Isostearic Acid | 0.35 | 86.3 |
| 9 | XANTHAN GUM | 0.25 | 8.3 |
| 10 | HYDROXYETHYLCELLULOSE | 0.25 | 39.6 |
| 11 | CARBOMER | 0.20 | 1.7 |

Formulation 6, which contains Isostearic acid as the thickener, has its transmittance very close to that of control formulation 5, which is consistent with the photograph in FIG. 1.

Formulation 11 with carbomer as the thickener showed most hazy appearance.

Example 2

Figure 3:
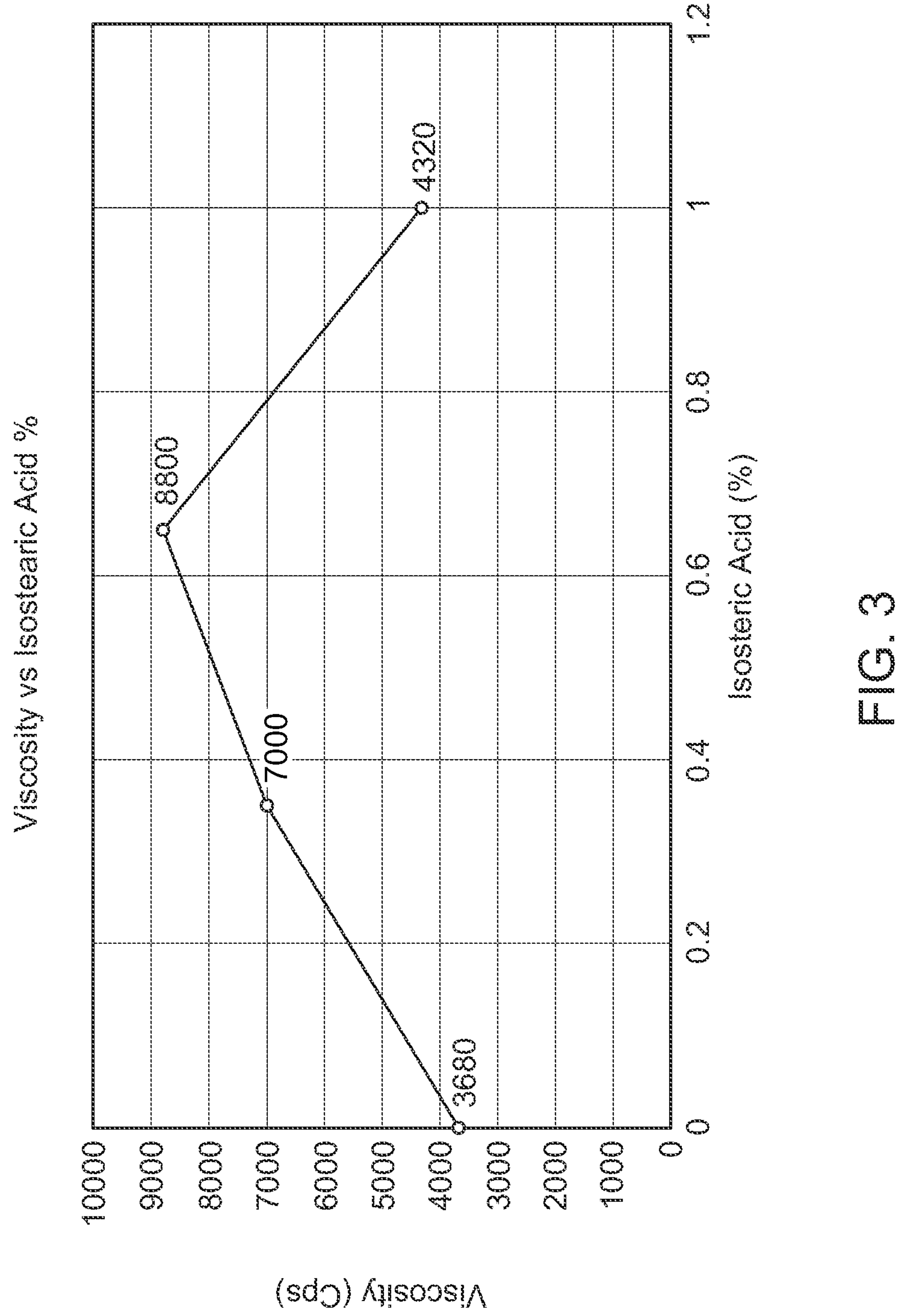
FIG. 3 is a chart showing viscosity versus a percentage of isostearic acid.

According to Example 1, isostearic acid as a thickening agent can thicken a cleanser formulation into a clear jelly. To determine a relationship between an amount of isostearic acid and viscosity, formulations with three different concentrations of isostearic acid were studied in comparison to control formulation 5. The compositions of the formulations are listed in Table 4. The results are presented in Table 5 and FIG. 3.

TABLE 4

| Compositions of cleanser formulations | | | | | | |
|---|---|---|---|---|---|---|
| RM Code | Trade Name | INCI Name | FL #5 W/W %* | FL #6 W/W %* | FL #7 W/W %* | FL #8 W/W %* |
| Solvent | DEIONIZED WATER | WATER | 42.84 | 42.55 | 42.30 | 41.90 |
| Emollient | GLYCERINE 99.7%/MB | GLYCERIN | 6.00 | 6.00 | 6.00 | 6.00 |
| Surfactant | PUREACT WS CONC | WATER & SODIUM METHYL COCOYL TAURATE | 8.00 | 8.00 | 8.00 | 8.00 |
| | POLY SUGA ®NATE 160P NC MB | WATER & SODIUM HYDROXYPROPYLSULFONATE LAURYLGLUCOSIDE CROSSPOLYMER & SODIUM CHLORIDE | 10.00 | 10.00 | 10.00 | 10.00 |
| | TRITEXAINE CB-HP | WATER & COCAMIDOPROPYL BETAINE & SODIUM CHLORIDE & GLYCERIN | 5.00 | 5.00 | 5.00 | 5.00 |

TABLE 4-continued

Compositions of cleanser formulations

| RM Code | Trade Name | INCI Name | FL #5 W/W %* | FL #6 W/W %* | FL #7 W/W %* | FL #8 W/W %* |
|---|---|---|---|---|---|---|
| | COLA ®TERIC CBS-HP MB | WATER & COCAMIDOPROPYL HYDROXYSULTAINE & SODIUM CHLORIDE & TETRASODIUM GLUTAMATE DIACETATE | 20.00 | 20.00 | 20.00 | 20.00 |
| | PLANTAREN ® 818 UP | COCO-GLUCOSIDE & WATER | 6.00 | 6.00 | 6.00 | 6.00 |
| Co-surfactant/ thickener | ISOSTEARIC ACID EX | ISOSTEARIC ACID | 0.00 | 0.35 | 0.65 | 1.00 |
| Preservative | BOTANISTAT PF-64 | PHENOXYETHANOL & CAPRYLYL GLYCOL & ETHYLHEXYLGLYCERIN & HEXYLENE GLYCOL | 1.00 | 1.00 | 1.00 | 1.00 |
| | KALAMA ® SODIUM BENZOATE NF/FCC | SODIUM BENZOATE | 0.30 | 0.30 | 0.30 | 0.30 |
| pH adjust | CITRIC ACID ANHYDROUS (USP) (RM-253) | CITRIC ACID | 0.86 | 0.80 | 0.75 | 0.80 |
| | | Total | 100.00 | 100.00 | 100.00 | 100.00 |

*W/W % means percent weight (mass) within the composition

The compositions in Table 4 were prepared as follows:

Water was added in a main beaker and mixing started with a propeller. The content of the main beaker was heated up to 65-75 C.

In a separate beaker, glycerin was mixed with the preservative until uniform. Then the content of the separate beaker was added to the main beaker.

While mixing the content of the main beaker, isostearic acid was added

Temperature was checked to be maintained at 65-75 C

Each of surfactants was added to the main beaker one by one. After each addition, the content of the main beaker was mixed until uniform. The same temperature was maintained between additions.

citric acid anhydrous was added to the main beaker to adjust pH

TABLE 5

Viscosity vs isostearic acid concentration

| | Isostearic Acid % | Viscosity(cps) (LV#3,12 rpm) |
|---|---|---|
| 5 | 0 | 3680 |
| 6 | 0.35 | 7000 |
| 7 | 0.65 | 8800 |
| 8 | 1.00 | 4320 |

Figure 4:
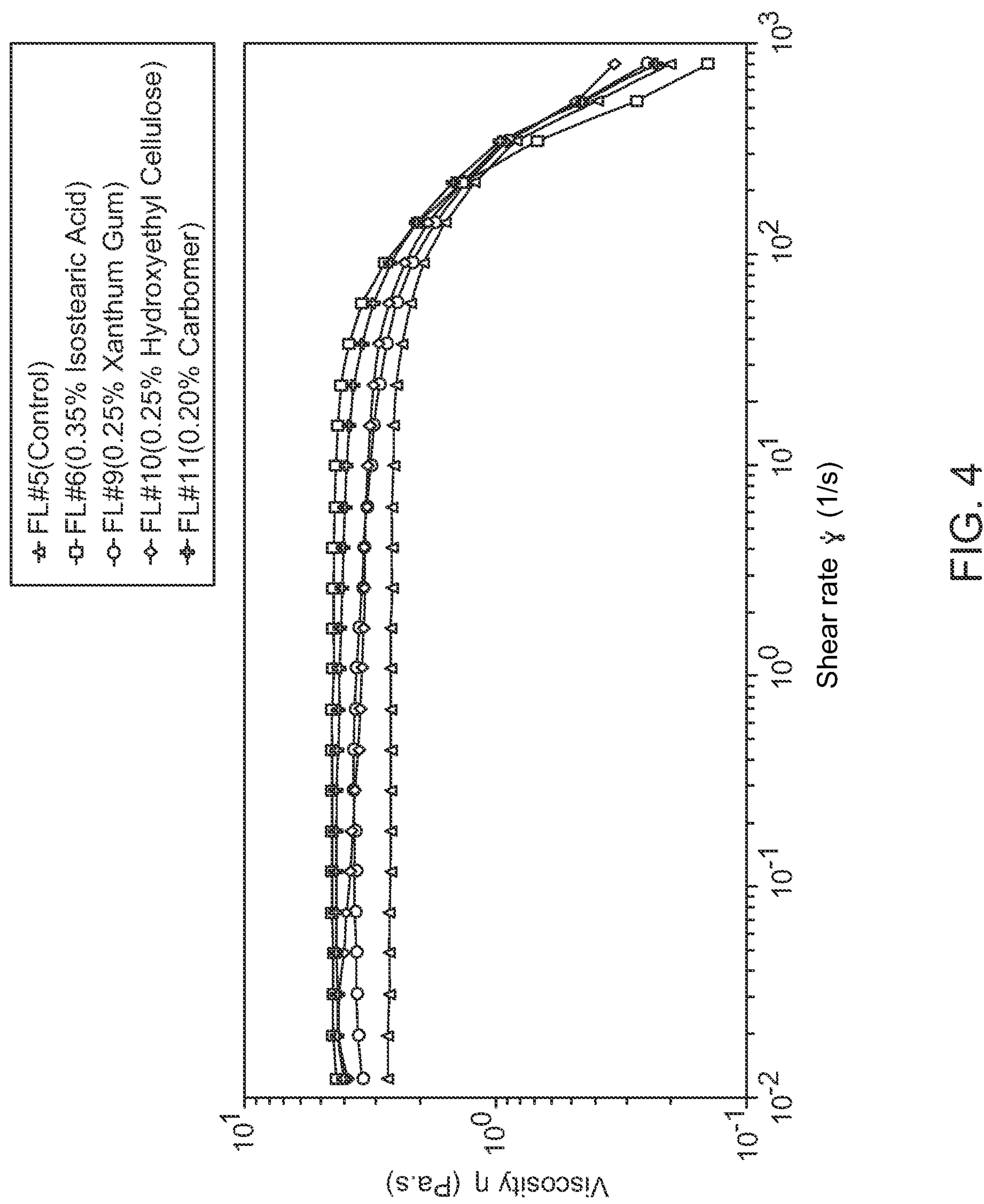
FIG. 4 is a plot of viscosity versus a shear rate.

Table 5 and FIG. 4 show the relationship between an isostearic acid concentration and viscosity.

Isostearic acid concentration may be from about 0.3% to about 0.8% to provide a desirable viscosity.

The above experiments confirmed that isostearic acid as a thickening agent can thicken cleanser formulations into a clear jelly.

The four formulations from Table 4, including the formulations 6-8 with three different concentrations of isostearic acid and the control formulation 5 with no thickener, have been monitored for 4 weeks at multiple conditions. The results in Table 6 and Table 7 show that viscosity and pH of all the formulations is consistent at all the temperature after 4 weeks.

The formulations 6-8 maintained the clarity in the same manner as the control formulation 5.

TABLE 6

Stability after storing for weeks at various temperatures. Viscosity is in centipoise (cps)

| Viscosity @4 weeks | 5 (CLEAR) Isostearic Acid @0% | 6 (CLEAR) Isostearic Acid @0.35% | 7 (CLEAR) Isostearic Acid @0.65% | 8 (CLEAR) Isostearic Acid @1.0% |
|---|---|---|---|---|
| −5° C. | 3760 | 4850 | 9520 | 5440 |
| 0° C. | 3640 | 6920 | 10,080 | 5220 |
| 25° C. | 3880 | 7840 | 10,080 | 4920 |
| 37° C. | 3760 | 7420 | 10,160 | 5320 |
| 45° C. | 3840 | 6820 | 9920 | 5790 |
| 50° C. | 3720 | 6820 | 10,120 | 5340 |

TABLE 7

Stability after storing for weeks at various temperatures. pH.

| pH @4 weeks | 5 (CLEAR) Isostearic Acid @0% | 6 (CLEAR) Isostearic Acid @0.35% | FL#7 (Clear) Isostearic Acid @0.65% | FL#8 (Clear) Isostearic Acid @1% |
|---|---|---|---|---|
| −5° C. | 5.22 | 5.31 | 5.27 | 5.28 |
| 0° C. | 5.22 | 5.25 | 5.30 | 5.25 |
| 25° C. | 5.22 | 5.26 | 5.30 | 5.26 |
| 37° C. | 5.23 | 5.27 | 5.31 | 5.26 |
| 45° C. | 5.23 | 5.27 | 5.32 | 5.27 |
| 50° C. | 5.23 | 5.27 | 5.33 | 5.27 |

Example 3

Flow properties of the five cleanser formulations, including control formulation 5, see Table 8, were compared by Rheometer. Shear Rate Range: 0.01 to 1000 (l/s). The results are in FIG. 4.

TABLE 8

| Formulation # | Thickener INCI Name | Mass % |
|---|---|---|
| 5 | none | 0 |
| 9 | XANTHAN GUM | 0.25% |
| 10 | HYDROXYETHYLCELLULOSE | 0.25% |

TABLE 8-continued

| Formulation # | Thickener INCI Name | Mass % |
|---|---|---|
| 11 | CARBOMER | 0.20% |
| 6 | Isostearic Acid | 0.35% |

Table 9 reports rheology data for formulations 5, 6 and 9-11

All the formulations containing a thickener, i.e. formulations 6 and 9-11, showed similar flow pattern in the low to medium shear range with a relative higher yield. This may indicate a slow flowable texture before applying the formulation. The control formulation 5 had a low viscosity at low shear rate, which will result in drip or run when applying the formulation.

Formulation 6 with isostearic acid showed most shear thinning property at the higher share range, such as 90 l/s. This demonstrates that formulation 6 will have a good performance during the application. In other words, cleansing formulation 6 is easy to apply and rinse.

TABLE 9

| Rheology Data at Low(4 1/s) and High(90 1/s) Shear Viscosity(Pa*s) | | |
|---|---|---|
| Sample | Viscosity at Shear Rate 4(1/s) | Viscosity at Shear Rate 90(1/s) |
| FL #5(Control) | 2.6 | 1.9 |
| FL #6 | 3.3(+27%) | 2.8(+47%) |
| FL #9 | 3.4(+31%) | 2.2(+16%) |
| FL #10 | 4.1(+58%) | 2.3(+21%) |
| FL #11 | 4.4(+69%) | 2.6(+37%) |

Example 4

Results of customer evaluations of cleansing formulations with isostearic acid as a thickener, such as Formulations 6 and 7, are presented in Table 10.

Customers received the following instructions for applying the cleansing formulations:

Application area: whole face.

Test product application method: squeeze proper amount of the cleansing gel into a palm and gently massage into a wet or dry skin. Add some water to bubble. Rinse well and pat dry. Avoid direct contact with eyes. Frequency of use: use every evening, and not use the cleansing product in the morning. Duration of use: use continuously for 28 days.

Number of subjects: 27

Age range: 24-60

Skin type: all

Skin hydration on inner forearm was measured by Corneometer, CM825 was 15~45 (Corneometer Unit, C.U.) during process of screening and baseline value (TO) measurement; Any cosmetics or drugs was used on test sites within 3 days Application area: Inner forearm Test product application method: 1. the skin of the test site was wetted with water 2. According to the random table, the test product was be evenly applied in a single dose of (2.0±0.1) mg/cm$^2$ with the disposable latex finger covers, then gently applied to produce foam and massages gently; 3. Rinsed off with clean water and dried remaining water on the skin with clean facial tissues; 4. The blank control area did not use any product; however, the same treatment and operation was carried out as the same as the test product. Frequency of use: Single use The formulation used in the evaluation was similar to the formulation #7. The formulation used in the evaluation contains all ingredients of the formulation #7.

TABLE 10

| Consumer Perception Assessment | % Top two responses (Strongly agree & Agree) 5 minutes | 4 weeks |
|---|---|---|
| 1. Test product is easy to wash. | 94.55% | 96.36% |
| 2. Skin is not slippery after washing skin. | 92.73% | 96.36% |
| 3. Skin feel is not dry after cleaning skin. | 98.18% | 100.00% |
| 4. Skin feels no tight after using. | 94.55% | 96.36% |
| 5. Test product is no residue after cleaning skin. | 96.36% | 98.18% |
| 6. Test product is mild. | 98.18% | 98.18% |
| 7. Skin feels moisturized and clear after washing. | 92.73% | 96.36% |
| 8. Skin feels soothing after washing. | 94.55% | 96.36% |
| 9. Test product is no irritation after using. | 100.00% | 100.00% |
| 10 Test product are fined and low foaming. | 94.55% | 96.36% |
| 11. Test product is skin-friendly. | 94.55% | 96.36% |
| 12. Skin feels water-oil balance after using product. | 92.73% | 94.55% |
| 13. Cleaning effect of test product is just right. | 96.36% | 98.18% |
| 14 Skin becomes soft. | 96.36% | 98.18% |
| 15. Skin becomes healthier. | 92.73% | 94.55% |
| 16. Skin becomes purer. | 96.36% | 98.18% |
| 17. Skin becomes clearer and more transparent. | 87.27% | 94.55% |
| 18. Skin feels fresh. | 98.18% | 98.18% |
| 19. Test product can remove light makeup (eyes, face, lips). | 90.91% | 94.55% |
| 20. Pores become clear | 96.36% | 98.18% |
| 21. Skin feels no irritation when removing makeup from eye area | 100.00% | 100.00% |

TABLE 10-continued

| | Consumer Perception Assessment | % Top two responses (Strongly agree & Agree) 5 minutes | 4 weeks |
|---|---|---|---|
| 22. | Test product has soothing effect after using product | 87.27% | 96.36% |
| 23. | Test product has moisturizing effect after using product. | 92.73% | 98.18% |

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A cosmetic composition, comprising about 0.3 mass % to about 0.8 mass % of isostearic acid; about 2 mass % to about 8 mass % Sodium Hydroxypropylsulfonate Laurylglucoside Crosspolymer; about 2.5 mass % to about 5 mass % of coco-glucoside; 1 mass % to 3 mass % of cocamidopropyl betaine and at least 40 mass % of water.

2. The cosmetic composition of claim 1, wherein a mass ratio between the Sodium Hydroxypropylsulfonate Laurylglucoside Crosspolymer and the isostearic acid is from 2.5 to 27.

3. The cosmetic composition of claim 1, further comprising a taurate surfactant.

4. The cosmetic composition of claim 3, wherein the taurate surfactant is Sodium Methyl Cocoyl Taurate.

5. The cosmetic composition of claim 3, wherein an amount of the taurate surfactant in the cosmetic composition is from about 0.5 mass % to about 6 mass %.

6. The cosmetic composition of claim 3, wherein a mass ratio between the taurate surfactant and the isostearic acid is from 0.3 to 30.

7. The cosmetic composition of claim 1, wherein a mass ratio between the coco-glucoside and the isostearic acid is from 2.5 to 17.

8. The cosmetic composition of claim 1, further comprising cocamidopropyl hydroxysultaine.

9. The cosmetic composition of claim 8, wherein an amount of cocamidopropyl hydroxysultaine in the cosmetic composition is from 5 mass % to 20 mass %.

10. The cosmetic composition of claim 8, wherein a mass ratio between cocamidopropyl hydroxysultaine and the isostearic acid is from 6 to 40.

11. The cosmetic composition of claim 1, which is free of polyethylene glycol.

12. The cosmetic composition of claim 1, further comprising about 1 mass % to about 3 mass % of a taurate surfactant and 5 mass % to 12 mass % of cocamidopropyl hydroxysultaine.

13. The cosmetic composition of claim 1, wherein the cosmetic composition is a cleanser composition.

14. The cosmetic composition of claim 1, having a viscosity of from about 5000 cps to about 10000 cps.

15. A cosmetic method comprising applying the cosmetic composition of claim 1 to a keratinous surface of a subject.

16. The cosmetic composition of claim 12, having a viscosity of from about 5000 cps to about 10000 cps.

* * * * *